(12) United States Patent
Roth et al.

(10) Patent No.: US 6,517,239 B1
(45) Date of Patent: Feb. 11, 2003

(54) TIME-TEMPERATURE INDICATORS ACTIVATED WITH THERMAL TRANSFER PRINTING AND METHODS FOR THEIR PRODUCTION

(75) Inventors: Joseph D. Roth, Springboro, OH (US); John C. Rosenbaum, Dayton, OH (US)

(73) Assignee: NCR Corproation, Dayton, OH (US)

( * ) Notice: Subject to any disclaimer, the term of this patent is extended or adjusted under 35 U.S.C. 154(b) by 0 days.

(21) Appl. No.: 09/302,479

(22) Filed: Apr. 30, 1999

(51) Int. Cl.[7] .......................... B41J 31/06; B41M 7/00; G01N 31/22
(52) U.S. Cl. .................. 374/102; 376/104; 376/106; 116/206; 347/221; 503/201
(58) Field of Search ................................. 374/102, 104, 374/106; 116/206; 503/201; 428/484, 195; 347/171, 221

(56) References Cited

U.S. PATENT DOCUMENTS

| | | | |
|---|---|---|---|
| 3,663,278 A | | 5/1972 | Blose et al. |
| 3,857,821 A | * | 12/1974 | Becker et al. ............. 526/285 |
| 3,942,467 A | | 3/1976 | Witonsky |
| 3,999,946 A | | 12/1976 | Patel et al. |
| 4,189,399 A | | 2/1980 | Patel |
| 4,208,186 A | | 6/1980 | Patel |
| 4,212,153 A | | 7/1980 | Kydonieus et al. |
| 4,220,747 A | | 9/1980 | Preziosi et al. |
| 4,228,126 A | | 10/1980 | Patel et al. |
| 4,235,108 A | | 11/1980 | Patel |
| 4,238,352 A | | 12/1980 | Patel |
| 4,276,190 A | | 6/1981 | Patel |
| 4,298,348 A | | 11/1981 | Ivory |
| 4,315,643 A | | 2/1982 | Tokunaga et al. |
| 4,339,240 A | | 7/1982 | Patel |
| 4,389,217 A | | 6/1983 | Baughman et al. |
| 4,399,209 A | * | 8/1983 | Sanders et al. ............ 430/138 |
| 4,403,224 A | | 9/1983 | Wirnowski |
| 4,463,034 A | | 7/1984 | Tokunaga et al. |
| 4,523,207 A | | 6/1985 | Lewis et al. |
| 4,533,640 A | | 8/1985 | Shafer |
| 4,628,000 A | | 12/1986 | Talvalkar et al. |
| 4,687,701 A | | 8/1987 | Knirsch et al. |
| 4,698,268 A | | 10/1987 | Ueyama |
| 4,707,395 A | | 11/1987 | Ueyama et al. |
| 4,737,463 A | | 4/1988 | Bhattacharjee et al. |
| 4,777,079 A | | 10/1988 | Nagamoto et al. |
| 4,778,729 A | | 10/1988 | Mizobuchi |
| 4,812,053 A | * | 3/1989 | Bhattacharjee ............... 374/102 |
| 4,869,941 A | | 9/1989 | Ohki |
| 4,917,503 A | * | 4/1990 | Bhattacharjee ............... 374/102 |
| 4,923,749 A | | 5/1990 | Talvalkar |
| 4,931,420 A | | 6/1990 | Asano et al. |
| 4,975,332 A | | 12/1990 | Shini et al. |
| 4,983,446 A | | 1/1991 | Taniguchi et al. |
| 4,988,563 A | | 1/1991 | Wehr |
| 5,047,455 A | * | 9/1991 | Hesse et al. ................. 523/508 |
| 5,057,434 A | * | 10/1991 | Prusik et al. ............... 116/206 |
| 5,128,308 A | | 7/1992 | Talvalkar |
| 5,236,886 A | * | 8/1993 | Tsuchiya et al. ............ 428/195 |
| 5,240,781 A | | 8/1993 | Obata et al. |
| 5,248,652 A | | 9/1993 | Talvalkar |
| 5,420,000 A | | 5/1995 | Patel et al. |
| 5,476,792 A | | 12/1995 | Ezrielev et al. |
| 6,011,573 A | * | 1/2000 | Nagahamaya et al. ...... 347/217 |

FOREIGN PATENT DOCUMENTS

| | | |
|---|---|---|
| EP | 0047918 | 3/1982 |
| EP | 0117390 | 9/1984 |
| EP | 1048476 A1 * | 11/2000 |
| EP | 1048477 A1 * | 11/2000 |

\* cited by examiner

Primary Examiner—David Martin
Assistant Examiner—Jeanne-Marguerite Goodwin
(74) Attorney, Agent, or Firm—Millen White Zelano & Branigan PC

(57) ABSTRACT

Time-temperature indicators (TTIs) which are generated by converting indicator compounds from an inactive state to an active state using a thermal transfer printing apparatus are described.

28 Claims, 1 Drawing Sheet

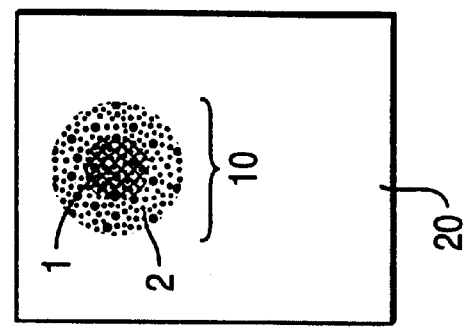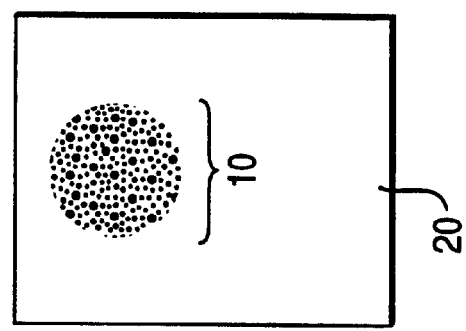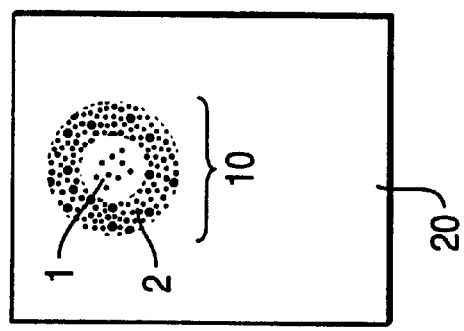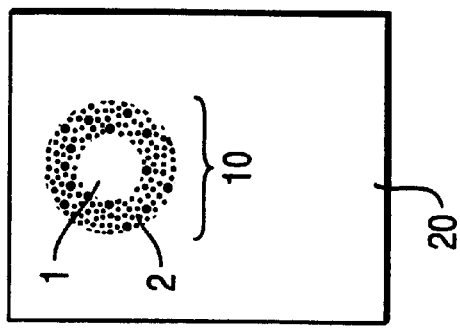

TIME-TEMPERATURE INDICATORS ACTIVATED WITH THERMAL TRANSFER PRINTING AND METHODS FOR THEIR PRODUCTION

BACKGROUND OF THE INVENTION

The invention relates to the field of time-temperature indicators (TTIs). TTIs are colorimetric labels which respond to cumulative exposure to time and temperature. TTIs provide a visual indicator that gradually changes with time, typically faster at elevated temperatures and slower at colder temperatures.

TTIs are attached to perishable products at the time of production to monitor the cumulative time/temperature exposure. TTIs are used for monitoring time and temperature exposure of a wide variety of items including perishables in-transit, consumer packages, and medical perishables. TTIs are typically more reliable in monitoring the remaining shelf life of a perishable product than expiration dates such as "sell-by" or "use-by" dates. Expiration dates assume a certain temperature history, and temperature histories that vary from this assumption result in either the sale of a spoiled product or the premature disposal of a good product. In contrast, TTIs respond directly to the temperature history of the product.

TTIs are commonly attached to shipping boxes for use by commercial distributors in the distribution of food and pharmaceuticals. The most common use is to ensure the integrity of the cold chain up to the supermarket.

Prepared TTIs have the disadvantage in that they must be stored at low temperatures or protected from actinic radiation prior to use. This requirement greatly increases the cost of production of TTIs and introduces an element of uncertainty as to the reliability of the indicators. Therefore, there is a need for TTI labels that can be activated at the site of application, thereby obviating a need for protection of the labels prior to use.

SUMMARY OF THE INVENTION

In accordance with this invention, there is provided a thermal transfer medium which is suitable for use in a thermal transfer printing apparatus and which contains at least one indicator compound within a thermal transfer layer of the thermal transfer medium which is convertible from an inactive state to an active state by the application of heat. The indicator compound may be transferred to a recording medium with a portion of the thermal transfer layer and converted from an inactive state to an active state by the application of heat in the thermal transfer printing apparatus, thereby forming a time-temperature indicator. The terms "time-temperature indicator' and "TTI', as used herein, refer to any calorimetric label which responds to an exposure element in a manner that indicates the degree of exposure to that element. Exposure elements include, for example, time, air, visible light, temperature, actinic radiation, and atomic radiation.

Also in accordance with this invention, a method of generating a time-temperature indicator (TTI) is provided as well as the time-temperature indicators produced. The method entails providing a thermal transfer medium suitable for use in a thermal transfer printing apparatus, wherein a thermal transfer layer of said medium contains at least one indicator compound. The method also entails heating the thermal transfer medium in the thermal transfer printing apparatus to a temperature sufficient to transfer the thermal transfer layer of the medium to a receiving substrate and convert the indicator compound within the thermal transfer layer from an inactive state to an active state. Once in the active state, the indicator compounds serve to monitor the exposure of the time-temperature indicator to various exposure elements.

A thermal transfer medium, which contains an inactive form of an indicator compound within a thermal transfer layer, can be manufactured, stored and shipped under normal conditions without resort to refrigerated and light-protected environments. The indicator compound can then be activated when desired through processing in a thermal transfer printing apparatus to generate a time-temperature indicator.

Indicator Compounds

Indicator compounds that are contemplated as part of this invention are any compounds which exhibit detectable changes in response to an exposure element, which may be converted from an inactive state to an active state through the application of heat from the print head of a thermal transfer printing apparatus and which can be incorporated in a thermal transfer layer of a thermal transfer medium and transferred to a receiving substrate. Preferred compounds are kinetic indicator compounds which provide a change in color (typically darken) from a chemical reaction in response to the exposure elements of interest such as the integrated time-temperature exposure of a product or article. The use of kinetic indicator compounds which respond to visible light, air, actinic radiation or atomic radiation and the TTIs prepared therewith, are also considered a part of this invention.

A preferred temperature range for integrated TTIs responding to both time and temperature, or for TTIs, which respond primarily to temperature will depend on their intended use. Where the TTI is to detect thawing, a range from about 0° C. and above is preferred. Where the TTI is to detect freezing, a range of about 0° C. and below is preferred. Manipulation of the response to different temperatures can be accomplished through the selection of indicator compounds and additives known in the art.

Preferred wavelength and intensity ranges for TTIs, which respond primarily to actinic radiation, will also depend on the intended use of the TTI. For example, where the TTI is intended to detect the exposure of film to harmful radiation, the TTI may be responsive to x-rays, UV light and visible light. Manipulation of the response to radiation at different wave lengths and intensities can be accomplished through the selection of indicator compounds and additives known in the art.

It is contemplated that activation of indicator compounds by processing of a thermal transfer medium in a thermal transfer printing apparatus may occur by various mechanisms including, for example, the following: melt recrystallization of the compounds to transform inactive compounds into active compounds, the application of heat to combine more than one indicator compound wherein the combination of the indicator compounds (such as from separate thermal transfer layers) results in the activation of the compounds, the activation of an initiator compound which catalyzes the polymerization of the indicator compounds. A preferred method of activation is by melt recrystallization. As another example, two different indicator compounds may be present in encapsulated form within the thermal transfer layer, wherein the compounds are able to mix and polymerize only after the application of heat has released the encapsulated forms. As a further example, substantially inactive compounds may be converted to substantially active compounds through heat activation of an initiator compound. For example, peroxides, which thermally decompose into free radicals, may be employed as an initiator compound to convert substantially inactive compounds into substantially active compounds.

Preferred temperature ranges for conversion of the indicator compounds from the inactive state to the active include those typically applied to a thermal transfer medium by the print head of a thermal transfer printing apparatus. For example, the temperature is preferably between 50° C. and 300° C., more preferably between 75° C. and 250° C.

Particularly preferred compounds that are contemplated as part of this invention are acetylenic compounds having at least two conjugated acetylene groups (—C≡C—C≡C—) per molecule. The manufacture and use of acetylenic compounds as time-temperature indicators are described in the following U.S. Patents, all of which are hereby incorporated by reference: U.S. Pat. No. 3,999,946 (Patel et al.); U.S. Pat. No. 4,220,747 (Preziosi et al.); U.S. Pat. No. 4,189,399 (Patel); U.S. Pat. No. 4,228,126 (Patel et al.); U.S. Pat. No. 4,208,186 (Patel); U.S. Pat. No. 4,235,108 (Patel); U.S. Pat. No. 4,276,190 (Patel); U.S. Pat. No. 4,298,348 (Ivory); U.S. Pat. No. 4,339,240 (Patel); U.S. Pat. No. 4,238,352 (Patel); U.S. Pat. No. 4,389,217 (Baughman et al.); U.S. Pat. No. 4,737,463 (Bhattacharjee et al.).

As described in U.S. Pat. Nos. 4,228,126 and 4,298,348, an inactive form of a diacetylene can exist at ambient temperature and ambient light conditions for indefinitely long periods of time. The inactive form can be subjected to gamma radiation at room temperature or thermal annealing below its melting point, without being converted to an active form. The inactive form can be converted by melt recrystallization into an active form, which can undergo 1,4-addition polymerization that results in a brightly colored polymer.

Several crystalline inactive and crystalline active forms of a diacetylene compound, of the same chemical composition, may exist. In such cases these inactive and active forms will exhibit the same general properties for "the active form" and "the inactive form", respectively, as described herein, and are included within the scope of this invention.

Diacetylene compounds, which are applicable in the invention, are also adequately described in U.S. Pat. No. 3,999,946. Generally, cyclic or acyclic diacetylenes, containing at least two conjugated —C≡C— groups, are applicable in the invention including symmetrically or unsymmetrically substituted diynes, triynes, tetraynes and hexaynes. In addition, mixtures of diacetylenes or co-crystallized compositions of diacetylenes, as described in U.S. Pat. No. 4,189,399, can be employed. In the simplest case, diacetylenes are of the form R—C≡C—C≡C—R', where R or R' can be the same or different substituent groups. Examples of R or R' groups include alkyl, aryl, benzoate, sulfonate, urethane, acid, alcohol, and carbazolyl. Preferred derivatives include mono and bisulfonates, mono and bisurethanes, mono and bisacids, mono and bisalcohols, and mono and bis carbazolyl derivatives of acetylenic compounds. Such preferred compounds, and derivatives thereof, are most useful as integrated time-temperature history indicators or integrated radiation-dosage history indicators over the time and temperatures likely to be experienced by commercial, perishable products. Examples of acetylenic compounds useful as indicators in this invention include the following:

2,4-hexadiyn-1,6-diol bis(phenylurethane) (HDDPU)
2,4-hexadiyn-1,6-diol bis(p-methoxybenzene sulfonate) (PMOBS)
9-(N-carbazolyl)-5,7-nonadiyn-1-ol phenylurethane (PUCNDO)
o,o'-diacetylenyldiphenyl glutarate (DADPG)
2,4-hexadiyn-1,6-diol-bis-p-toluene sulfonate
2,4-hexadiyn-1,6-diol-bis-(p-chlorobenzene sulfonate)

Both the range of color change and the composition reactivity can be varied by codeposition of different acetylenic compounds (at least one of which contains at least two conjugated acetylene groups) or by the codeposition of one or more acetylenic compounds which contain at least two conjugated acetylene groups with one or more compounds which have similar molecular shape and polarity as the acetylenic compound, but which do not contain reactive acetylenic functionalities. Such codepositions can be from the vapor, melt or solution phases.

The thermal reactivity of acetylenic compounds of the invention can be increased by adding a suitable conventional polymerization enhancer. Examples of conventional enhancers include, but are not limited to, alkyl peroxides such as dicumyl peroxide, azo compounds such 2-t-butylazo-2-cyano propane, diacyl peroxides such as benzoyl peroxide, hydroperoxides such as cumene hydro peroxide, ketone peroxides such as cyclohexanone peroxide and peroxyesters such as t-butyl peroxyacetate. The thermal reactivity can be decreased by adding a suitable conventional polymerization inhibitor. Examples of polymerization inhibitors include, but are not limited to, quinones such as benzoquinone, and aromatic nitro-compounds such as m-nitrobenzene and 2,4-dinitrochlorobenzene.

In some cases, the acetylenic compounds are sensitive to exposure to short wavelength UV or UV-visible radiation. Therefore, in order to eliminate undesirable photo-induced reactions, it may be desirable to incorporate a filter material into the thermal transfer layer which may be transferred to the receiving substrate in conjunction with the indicator compound. The UV reactivity evident for certain acetylenic compounds is substantially eliminated by protecting such compounds from exposure with a UV-absorbing film over the acetylenic compound. Conventional UV stabilizers are also useful for this purpose. Examples of UV stabilizers include, but are not limited to, benzophenones such as 2-hydroxy-4-methoxy benzophenone, benzotrazoles such as 2-(2'-hydroxy-5'-methylphenyl)benzotriazole, substituted acrylates such as ethyl-2-cyano-3,3-diphenyl acrylate and aryl esters such as phenyl salicylate.

In order to obtain the widest possible range of indicator response from a thermal transfer layer after transfer, the thermal transfer layer can contain a mixture of different indicator compounds, each of which undergoes a series of color changes during thermal history development. Alternatively, the thermal transfer layer can consist of adjacent strips containing different acetylenic compositions. Such a thermal transfer layer can then be used to generate TTIs with strips of different sensitivity.

In particular instances, it may be convenient to apply the thermal transfer layer to the receiving substrate in the form of a printed message. In certain embodiments, this message will not be readable on the chosen background until the indicator compound darkens in color in response to an exposure element.

Preparation of Indicator Compounds

As described in U.S. Pat. Nos. 4,228,126 and 4,298,348, inactive forms of diacetylenes can generally be prepared by solvent recrystallization. In general, the inactive form of a diacetylene will be obtained from solution when very rapid precipitation conditions are employed. Typically, rapid precipitation will occur with rapid cooling of the solution, rapid evaporation of the solvent, or the addition of the solution to another liquid which is miscible with the solvent but acts as a non-solvent for the acetylenic compound.

The inactive form of a diacetylene can also be prepared by precipitating the inactive form of the compound from a solution at a rate sufficiently greater than the rate of precipitation of an active form of the compound, whereby substantially all of the precipitate obtained is the inactive form. In general, a solvent or a combination of solvents is chosen such that the diacetylene recrystallizes rapidly from the solvent material. For example, the inactive form of 9-(N-carbazolyl)-5,7-nonadiyn-1-ol phenylurethane (PUCNDO), is obtained when recrystallizing crude material from acetone and allowing the crystallization to occur rapidly; the active form results when the recrystallization is allowed to proceed slowly.

The crystalline inactive form of the cyclic diacetylene, o,o'-diacetylenyldiphenyl glutarate (DADPG), is obtained by rapid cooling of a (10:90) acetone/petroleum ether (b.p. 60–110° C.) solution, at a concentration of 0.007 g/ml at room temperature, with an ice-water bath. The inactive form of DADPG is not solid state polymerizable with gamma-radiation. Alternately, the active form of DADPG is obtained by slow solvent evaporation of a 10:90 acetone/petroleum ether solution, at the same concentration, at room temperature. The active form is polymerizable upon exposure to gamma radiation. The crystalline inactive form melts at 133–134 C., about 10° C. lower than the active form.

The inactive form of a diacetylene can be converted to the active form by heating the inactive form above its melting point, typically from about 1° C. to 20° C. above the melting point, and cooling the melt to room temperature. For example, the inactive form (colorless needles) of DADPG is heated to 150° C., about 16° C. to 17° C. above the melting point, and rapidly cooled to 25° C., resulting in an active form as red solids. By heating the inactive form of the indicator compounds at a temperature up to about 20° C. above its melting point, preferably from about 5° C. to about 15° C. above its melting point and then allowing the indicator compound to cool to room temperature (25° C.), the active form will generally be obtained.

The inactive form can also be prepared by spraying a solution of a diacetylene onto a substrate and allowing the solvent to evaporate rapidly. For example, spraying an acetone or tetrahydrofuran solution of 2,4-hexadiyn-1,6-diol bis(phenylurethane) (HDDPU) onto a substrate, and allowing the solvent to evaporate rapidly, for example, by passing a stream of air over the surface, results in the inactive form.

Thermal Transfer Medium

The term, "thermal transfer medium", as used herein, refers to any substrate coated with at least one thermal transfer layer, portions of which selectively transfer to a receiving substrate when heated by the print head of a thermal transfer printing apparatus. The thermal transfer ribbons of this invention have at least one thermal transfer layer which contains at least one inactive indicator compound which is activated when transferred to a receiving substrate using a thermal transfer printing apparatus. The thermal transfer medium may be, for example, in ribbon form or in sheet form. Any number of materials (resins, waxes, pigments) used in conventional thermal transfer layers may be employed in conjunction with this invention. Representative documentation of the materials used for thermal transfer layers as well as other aspects of thermal transfer printing, is found in the following U.S. Patents, all of which are incorporated herein by reference:

U.S. Pat. No. 3,663,278 (Blose et al.); U.S. Pat. No. 4,315,643 (Tokunaga et al.); U.S. Pat. No. 4,403,224 (Winowski); U.S. Pat. No. 4,463,034 (Tokunaga et al.); U.S. Pat. No. 4,523,207 (Lewis et al.); U.S. Pat. No. 4,628,000 (Talvalkar et al.); U.S. Pat. No. 4,687,701 (Knirsch et al.); U.S. Pat. No. 4,698,268 (Ueyama et al.); U.S. Pat. No. 4,707,395 (Ueyama et al.); U.S. Pat. No. 4,777,079 (Nagamoto); U.S. Pat. No. 4,778,729 (Mizobuchi); U.S. Pat. No. 4,869,941 (Ohki); U.S. Pat. No. 4,923,749 (Tavalkar); U.S. Pat. No. 4,975,332 (Shini et al.); U.S. Pat. No. 4,983,446 (Taniguchi et al.); U.S. Pat. No. 4,988,563 (Wehr); U.S. Pat. No. 5,128,308 (Talvalkar); U.S. Pat. No. 5,248,652 (Talvalkar et al.); U.S. Pat. No. 5,240,781 (Obatta et al.).

The substrate of the thermal transfer medium can be any material that provides sufficient rigid support for the thermal transfer layer and does not chemically interfere with the active or inactive forms of the indicator compound or the transfer of the indicator compounds to the receiving substrate. For example, substrates that may used as part of the thermal transfer medium in conjunction with this invention include polyesters such as polyethyleneterephthalate (PET).

Other components of the thermal transfer layer which may be mixed with the indicator compounds for transfer from the thermal transfer medium to the receiving substrate include, for example, substances that aid in adhesion to the receiving substrate, that aid in transfer to the receiving substrate, or that affect print quality. These substances include, for example, selected waxes, resins, dyes, pigments and substances that protect the indicator compounds from UV radiation.

The thermal transfer layer may optionally contain pigments or dyes that are transferred to the receiving substrate to generate an image in conjunction with the transfer and activation of indicator compounds to the receiving substrates. Additionally, the indicator compounds may themselves serve as dyes for generating an image on the receiving substrate. For example, the indicator compounds may initially form a light-colored image upon activation and transfer, wherein the image darkens with exposure to an exposure element such as, for example, time or temperature.

Receiving Substrate

The receiving substrate, as used herein, refers to any substrate suitable for receiving the thermal transfer layer containing indicator compounds from a thermal transfer medium through the application of heat by the print head in a thermal transfer printing apparatus. The receiving substrate may be an article of product packaging or the receiving substrate may be a label that can be readily affixed to a product before or after activation of the indicator compound. A preferred receiving substrate is a label with an adhesive backing. Preferred examples of receiving substrates which may be employed in conjunction with the invention include the following: coated and uncoated papers, cardboard, wood, metals and plastics.

Printers

The term, "thermal transfer printing apparatus", as used herein refers to any apparatus which is suitable for the selective application of thermal energy to activate and transfer indicator compounds from the thermal transfer layer of the thermal transfer medium to a receiving substrate. Conventional thermal transfer printers are suitable for use in this invention.

Use of Indicator Compounds

Particular indicator compounds may be matched to a particular perishable product or to another particular use. For example, the indicator compounds may be selected to parallel the response of a particular product to changes in temperature over time. Examples of perishable products for which the use of thermal printer activated indicator compounds may be useful include, for example, packaged fresh and frozen foods, dairy products, meat, pharmaceuticals, photographic film, canned goods, spices, vitamins, seeds, plants. Other products which slowly degrade over time and for which time-temperature indicators may be useful include, for example, paints, photographic film, coatings, adhesives, caulks etc. Time-temperature indicators could also be useful as sterilization indicators or as cooking indicators to indicate when a product is sterilized or finished cooking.

Processes monitored by indicator compounds may include undesirable processes such as, for example, degradation or spoilage of products or desirable processes such as, for example, ripening of produce.

BRIEF DESCRIPTION OF THE DRAWINGS

FIGS. 1A–1D illustrate the aging sequence of a time-temperature indicator of this invention.

FIG. 1A is a time temperature indicator (10) immediately after printing central portion (1) on receiving substrate (20) with a thermal transfer printing apparatus. Central portion (1) contains the activated indicator compounds and is initially light colored as compared to the outer ring (2), which is the reference color.

FIG. 1B illustrates TTI (10) of FIG. 1A sometime after printing central portion (1) on receiving substrate (20) and activation of the indicator compounds. Central portion (1) has darkened with time and temperature but is still lighter than the outer ring (2), indicating that the labeled product is still useable.

FIG. 1C shows TTI (10) of FIG. 1A with no discernable central portion or outer ring in that they are the same color. The product is still useable but must be used immediately.

FIG. 1D illustrates TTI (10) of FIG. 1A where usability of the product can not be guaranteed. Central portion (1) is darker than the outer ring (2).

The colored outer ring (2) may be preprinted or it may be generated with the thermal transfer printing apparatus at the same time as Central portion (1) is printed.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A thermal transfer medium, suitable for use in a thermal transfer printing apparatus, comprising at least one thermal transfer layer which contains at least one indicator compound,
    wherein the indicator compound exhibits detectable changes in response to an exposure element and wherein the indicator compound is convertible from an inactive state to an active state by the application of heat from a print head of said thermal transfer printing apparatus and wherein the indicator compound transfers to a receiving substrate with said thermal transfer layer.

2. A thermal transfer medium according to claim 1, wherein at least one indicator compound is an acetylene compound.

3. A thermal transfer medium according to claim 2, wherein at least one acetylene compound is selected from the group consisting of 2,4-hexadiyn-1,6-diol bis (phenylurethane); 2,4-hexadiyn-1,6-diol bis(p-methoxybenzene sulfonate); 9-(N-carbazolyl)-5,7-nonadiyn-1-ol phenylurethane; o,o'-diacetylenyldiphenyl glutarate; 2,4-hexadiyn-1,6-diol-bis-p-toluene sulfonate; 2,4-hexadiyn-1,6-diol-bis-(t-phenylazophenyl sulfonate); 2,4-hexadiyn-1,6-bis-(p-toluene sulfonate); and 2,4-hexadiyn-1,6-diol-bis-(p-chlorobenzene sulfonate.

4. A thermal transfer medium according to claim 1, wherein the indicator compound is convertible from an inactive state to an active state by melt recrystallization.

5. A thermal transfer medium according to claim 2, wherein said thermal transfer layer also contains a component that is a polymerization enhancer or a polymerization inhibitor for at least one indicator compound.

6. A thermal transfer medium according to claim 2, wherein at least one acetylene compound has two conjugated acetylene groups.

7. A thermal transfer medium according to claim 1, wherein the indicator compound is convertible from a substantially inactive state to an active state by activation of an initiator compound.

8. A thermal transfer medium according to claim 1, wherein the indicator compound is convertible in said thermal transfer printing apparatus with a print head operating at a temperature in the range of 75° C. to 275° C.

9. A thermal transfer medium according to claim 1, wherein said thermal transfer layer also contains dye components for forming an image on a receiving substrate.

10. A thermal transfer medium according to claim 1, wherein the indicator compound exhibits detectable changes in color in response to integrated time-temperature exposure when in an active state.

11. A thermal transfer medium according to claim 10, wherein the indicator compound in an activated state exhibits detectable changes in color in response to temperatures of 0° C. and above.

12. A thermal transfer medium according to claim 10, wherein the indicator compound in an activated state exhibits detectable changes in color in response to temperatures of 0° C. and below.

13. A thermal transfer medium according to claim 1, wherein the indicator compound in an activated state exhibits detectable changes in color in response to actinic radiation.

14. A thermal transfer medium according to claim 1, wherein the indicator compound in an activated state exhibits detectable changes in color in response to visible light, actinic radiation with a wavelength in the UV range, actinic radiation with a wavelength in the x-ray range or a combination thereof.

15. A method which comprises:
    providing a thermal transfer medium suitable for use in a thermal transfer printing apparatus comprising at least one thermal transfer layer which contains at least one indicator compound, wherein said indicator compound exhibits detectable changes in response to an exposure element, and wherein the indicator compound is convertible from an inactive state to an active state by the application of heat from a print head of said thermal transfer printing apparatus, and wherein the indicator compound transfers to a receiving substrate with said thermal transfer layer;

heating the thermal transfer medium in said thermal transfer printing apparatus to soften portions of the thermal transfer layer with said indicator compound and convert at least some of the indicator compound to an active state, and transferring softened portions of the thermal transfer layer which contains activated indicator compound to said receiving substrate to form a time-temperature indicator.

16. A method according to claim 15, wherein at least one indicator compound is an acetylene compound.

17. A method according to claim 16, wherein at least one acetylene compound is selected from the group consisting of 2,4-hexadiyn-1,6-diol bis(phenylurethane);2,4-hexadiyn-1,6-diol bis(p-methoxybenzene sulfonate);9-(N-carbazolyl)-5,7-nonadiyn-1-ol phenylurethane; o,o'-diacetylenyldiphenyl glutarate; 2,4-hexadiyn-1,6-diol-bis-p-toluene sulfonate; 2,4-hexadiyn-1,6-diol-bis-(t-phenylazophenyl sulfonate); 2,4-hexadiyn-1,6-bis-(p-toluene sulfonate); and 2,4-hexadiyn-1,6-diol-bis-(p-chlorobenzene sulfonate).

18. A method according to claim 16, wherein said thermal transfer layer also contains a component that is a polymerization enhancer or a polymerization inhibitor for at least one indicator compound.

19. A method according to claim 15, wherein the indicator compound is converted from an inactive state to an active state by melt recrystallization.

20. A method according to claim 15, wherein the indicator compound is converted from a substantially inactive state to an active state by activation of an initiator compound.

21. A method according to claim 15, wherein the indicator compound is converted from an inactive state to an active state by heating within said thermal transfer printing apparatus to a temperature in the range of 75° C. to 275° C.

22. A method according to claim 15, wherein said thermal transfer layer also contains dye components that are transferred to the receiving substrate to form an image.

23. A method according to claim 22, wherein at least one acetylene compound has two conjugated acetylene groups.

24. A method according to claim 15, wherein the indicator compound exhibits detectable changes in color in response to integrated time-temperature exposure when in an active state.

25. A method according to claim 24, wherein the indicator compound in an activated state exhibits detectable changes in color in response to temperatures of 0° C. and above, temperatures of 0° C. and below, visible light or actinic radiation.

26. A time-temperature indicator prepared by the method of claim 15.

27. A thermal transfer system comprising:

a thermal transfer medium comprising at least one thermal transfer layer which contains at least one indicator compound, a thermal transfer printing apparatus having a print head which transfers thermal transfer layers of thermal transfer media to a receiving substrate, one or more receiving substrates, suitable for receiving thermal transfer layers transferred from thermal transfer media by the print head of said thermal transfer printing apparatus, wherein the thermal transfer medium is of a size suitable for feeding in the thermal transfer printing apparatus and the thermal transfer layer will transfer to one or more of said receiving substrates in response to the print head of said thermal transfer printing apparatus, wherein the indicator compound exhibits detectable changes in response to an exposure element, and wherein the indicator compound is convertible from an inactive state to an active state by the application of heat from the print head of said thermal transfer printing apparatus, and wherein the indicator compound is transferred to the receiving substrate with said thermal transfer layer.

28. A method which comprises:

providing a thermal transfer medium suitable for use in a thermal transfer printing apparatus comprising at least one thermal transfer layer which contains at least one inactive indicator compound which is activated when transferred to a receiving substrate, wherein said indicator compound exhibits detectable changes in response to an exposure element, and wherein the indicator compound is convertible from an inactive state to an active state by the application of heat from a print head of said thermal transfer printing apparatus, and wherein the indicator compound transfers to the receiving substrate with said thermal transfer layer;

heating the thermal transfer medium in said thermal transfer printing apparatus to soften portions of the thermal transfer layer with said indicator compound and convert at least some of the indicator compound to an active state, and transferring softened portions of the thermal transfer layer which contains activated indicator compound to said receiving substrate to form a time-temperature indicator.

* * * * *